United States Patent
Jencks et al.

(10) Patent No.: US 10,591,095 B2
(45) Date of Patent: Mar. 17, 2020

(54) LOW CARRYOVER HIGH PRESSURE FLUIDIC FITTING

(71) Applicant: Waters Technologies Corporation, Milford, MA (US)

(72) Inventors: Robert A. Jencks, Mendon, MA (US); Mark W. Moeller, Norton, MA (US); Kenneth R. Plant, Leominster, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 16/275,406

(22) Filed: Feb. 14, 2019

(65) Prior Publication Data

US 2019/0178426 A1   Jun. 13, 2019

Related U.S. Application Data

(60) Continuation of application No. 15/095,427, filed on Apr. 11, 2016, now Pat. No. 10,260,662, which is a
(Continued)

(51) Int. Cl.
*F16L 19/06* (2006.01)
*F16L 19/02* (2006.01)
*G01N 30/60* (2006.01)

(52) U.S. Cl.
CPC ......... *F16L 19/061* (2013.01); *F16L 19/0206* (2013.01); *F16L 19/0212* (2013.01); *F16L 19/06* (2013.01); *G01N 30/6026* (2013.01)

(58) Field of Classification Search
CPC ......... F16L 21/007; F16L 21/02; F16L 21/04; F16L 19/07; F16L 19/06; F16L 19/061;
(Continued)

(56) References Cited

U.S. PATENT DOCUMENTS 1,912,299 A   5/1933   Parker
2,988,385 A   6/1961   Foelster et al.
(Continued)

FOREIGN PATENT DOCUMENTS

GB   2482175 A    1/2012
WO   2004025162 A2   3/2004
(Continued)

OTHER PUBLICATIONS

Extended European Search Report in related European Patent Application No. 19183611.3, dated Oct. 22, 2019; 9 pages.
(Continued)

*Primary Examiner* — Aaron M Dunwoody
(74) *Attorney, Agent, or Firm* — Schmeiser, Olsen & Watts LLP

(57) ABSTRACT

A fluidic coupling includes a compression screw having an axial bore, a threaded portion configured to engage a threaded bore of a coupling body, and a drive surface, a tube extending through the axial bore of the compression screw, the tube including a body and a fluidic channel extending through the body to a sealing end, the body including a pocket formed at the sealing end having a depth, a collet secured to an outer surface of the tube and having a first end configured to receive the drive surface of the compression screw, and a polymer seal having a channel to pass a fluid, the polymer seal including a flange portion and an insertion portion.

20 Claims, 8 Drawing Sheets

Related U.S. Application Data division of application No. 14/122,795, filed as application No. PCT/US2012/041220 on Jun. 7, 2012, now Pat. No. 9,334,989.

(60) Provisional application No. 61/498,664, filed on Jun. 20, 2011.

(58) Field of Classification Search
CPC .. F16L 19/065; F16L 19/0206; F16L 19/0212
USPC ................................ 285/353, 384, 385, 342
See application file for complete search history.

(56) References Cited

U.S. PATENT DOCUMENTS

| | | | |
|---|---|---|---|
| 3,409,314 A * | 11/1968 | Roe .................. | F16L 19/028 |
| | | | 285/18 |
| 3,434,744 A | 3/1969 | Yoke et al. | |
| 3,485,517 A | 12/1969 | Howe | |
| 4,026,803 A | 5/1977 | Abrahams et al. | |
| 4,281,679 A * | 8/1981 | Stearns .................. | F16K 15/04 |
| | | | 137/515.5 |
| 4,619,473 A | 10/1986 | Someya | |
| 4,690,437 A | 9/1987 | Anderson, Jr. | |
| 5,120,084 A | 6/1992 | Hashimoto | |
| 5,402,829 A | 4/1995 | Takikawa et al. | |
| 5,423,581 A | 6/1995 | Salyers | |
| 5,669,637 A * | 9/1997 | Chitty ................... | F16L 33/224 |
| | | | 285/342 |
| 6,158,780 A | 12/2000 | Schaldach | |
| 7,533,909 B2 | 5/2009 | Sausner et al. | |
| 7,784,838 B2 | 8/2010 | Levy | |
| 7,789,433 B2 | 9/2010 | Calnek | |
| 7,909,367 B2 | 3/2011 | Plant et al. | |
| 8,079,621 B2 | 12/2011 | Ferlin et al. | |
| 8,459,700 B2 * | 6/2013 | Gill ....................... | E21B 33/038 |
| | | | 166/242.6 |
| 8,573,653 B2 | 11/2013 | Gamache | |
| 8,696,038 B2 | 4/2014 | Nienhuis | |
| 8,740,261 B2 | 6/2014 | Ford et al. | |
| 9,334,989 B2 | 5/2016 | Jencks et al. | |
| 9,751,085 B2 | 9/2017 | Pa | |
| 9,804,134 B2 * | 10/2017 | Burger ............... | G01N 30/6004 |
| 2003/0107216 A1 | 6/2003 | Gibson | |
| 2004/0247255 A1 | 12/2004 | Rosenburg et al. | |
| 2007/0158942 A1 | 7/2007 | Keene | |
| 2011/0006519 A1 | 1/2011 | Weh | |
| 2011/0025047 A1 | 2/2011 | Zelechonok et al. | |
| 2011/0107823 A1 | 5/2011 | Dehmer | |
| 2013/0043677 A1 * | 2/2013 | Gibson .................. | F16L 19/061 |
| | | | 285/331 |
| 2013/0193683 A1 | 8/2013 | Seto et al. | |
| 2013/0298647 A1 * | 11/2013 | Falk-Jordan .......... | F16L 19/061 |
| | | | 73/61.55 |
| 2014/0130580 A1 | 5/2014 | McAdams et al. | |
| 2014/0196524 A1 | 7/2014 | Hirmer et al. | |
| 2015/0198567 A1 * | 7/2015 | Buerger ............. | G01N 30/6039 |
| | | | 285/347 |
| 2015/0300542 A1 | 10/2015 | Graham et al. | |
| 2015/0308989 A1 | 10/2015 | Hochgraeber et al. | |
| 2015/0369403 A1 | 12/2015 | Cormier et al. | |
| 2016/0305586 A1 * | 10/2016 | Graham .................. | F16L 15/08 |
| 2017/0254452 A1 * | 9/2017 | Stearns ............... | F16L 19/0206 |
| 2017/0268704 A1 * | 9/2017 | Graham .................. | F16L 15/08 |
| 2017/0356575 A1 * | 12/2017 | Buerger ................. | B01D 15/22 |
| 2018/0094753 A1 | 4/2018 | Leveille | |
| 2019/0264844 A1 * | 8/2019 | Stearns ............... | F16L 19/0231 |

FOREIGN PATENT DOCUMENTS

| | | |
|---|---|---|
| WO | 2010000324 A1 | 1/2010 |
| WO | 2010133192 A1 | 11/2010 |
| WO | 2011076244 A1 | 6/2011 |
| WO | 2012149930 A1 | 11/2012 |
| WO | 2013174421 A1 | 11/2013 |

OTHER PUBLICATIONS

International Search Report and Written Opinion in priority International Patent Application No. PCT/US12/041220, dated Aug. 6, 2012. 10 pages.
Partial Supplementary Search Report in counterpart European Patent Application No. 12802451.0, dated Jan. 28, 2015. 8 pages.
Extended Search Report in counterpart European Patent Application No. 17200343.6, dated Feb. 16, 2018. 6 pages.
Extended Search Report in counterpart European Patent Application No. 16186225.5, dated Dec. 19, 2016. 6 pages.
International Preliminary Report on Patentability in priority International Patent Application No. PCT/US12/041220, dated Jan. 9, 2014. 9 pages.

* cited by examiner

LOW CARRYOVER HIGH PRESSURE FLUIDIC FITTING

RELATED APPLICATION

This application is a continuation of U.S. patent application Ser. No. 15/095,427, filed Apr. 11, 2016, titled "Low Carryover High Pressure Fluidic Fitting," which is a divisional of U.S. patent application Ser. No. 14/122,795, filed Nov. 27, 2013, titled "Low Carryover High Pressure Fluidic Fitting," which is the national stage of International Application No. PCT/US12/41220, filed Jun. 7, 2012, titled "Low Carryover High Pressure Fluidic Fitting," which claims the benefit of the earlier filing date of U.S. Provisional Patent Application Ser. No. 61/498,664, filed Jun. 20, 2011, titled "Low Carryover High Pressure Fluidic Fitting," the entireties of which are incorporated herein by reference.

FIELD OF THE INVENTION

The invention relates generally to fluidic couplings for high pressure systems. More particularly, the invention relates to leak tight fluidic couplings with near zero unswept volume for liquid chromatography systems.

BACKGROUND

Chemical analysis systems can include fluidic paths that accommodate high pressures. For example, a liquid chromatography system, such as a system designed for ultra high performance liquid chromatography (UHPLC), can operate at pressures of 15,000 psi or greater. The fluidic paths in such systems often include tubing that is coupled to other components or tubing using a conventional coupling such as a standard compression fitting.

In general, several requirements exist to maintain suitable performance of the chemical analysis system. First, a secure fluidic seal between the coupled elements is required at a low leak rate determined by the desired performance of the chemical analysis system. In addition, the fluidic seal should be sufficiently stable to prevent the release and re-uptake of fluid containing chemical samples or mixtures of samples through the seal interface. Re-uptake can result in carryover, which can significantly degrade system performance. Finally, the unswept volume, or the physical space within the fluid path in which fluid can be trapped and not flushed out by fluid flow, should be minimized. Unswept volume typically occurs between the end of the tubing and the point of seal on a ferrule further back in the fitting assembly. Excessive unswept volume can also result in carryover.

SUMMARY

In one aspect, the invention features a fitting for coupling fluidic paths, comprising: a coupling body having a threaded bore extending into a tapered cavity and, and an inner bore extending from the tapered cavity that is narrower than the threaded bore, the inner bore having a sealing surface at an end opposite to the tapered cavity, the coupling body having a channel extending from the sealing surface to pass a fluid; a compression screw having an axial bore, a threaded portion in engagement with the threaded bore of the coupling body, and a drive surface; a tube extending through the axial bore of the compression screw, the tube including a body and a fluidic channel extending through the body to a sealing end, wherein the body includes a pocket formed at the sealing end having a depth; a collet secured to an outer surface of the tube and having a first end configured to receive the drive surface of the compression screw; and a polymer seal having a channel to pass a fluid, the polymer seal including a flange portion and an insertion portion, wherein the insertion portion is located within the pocket of the body of the tube.

In another embodiment, the invention features a fluidic coupling comprising: a compression screw having an axial bore, a threaded portion configured to engage a threaded bore of a coupling body, and a drive surface; a tube extending through the axial bore of the compression screw, the tube including a body and a fluidic channel extending through the body to a sealing end, wherein the body includes a pocket formed at the sealing end having a depth; a collet secured to an outer surface of the tube and having a first end configured to receive the drive surface of the compression screw; and a polymer seal having a channel to pass a fluid, the polymer seal including a flange portion and an insertion portion, wherein the insertion portion is located within the pocket of the body of the tube.

In another embodiment, the invention features a method comprising: providing a fitting for coupling fluidic paths, the fitting including: a coupling body having a threaded bore extending into a tapered cavity and, and an inner bore extending from the tapered cavity that is narrower than the threaded bore, the inner bore having a sealing surface at an end opposite to the tapered cavity, the coupling body having a channel extending from the sealing surface to pass a fluid; a compression screw having an axial bore, a threaded portion in engagement with the threaded bore of the coupling body, and a drive surface; a tube extending through the axial bore of the compression screw, the tube including a body and a fluidic channel extending through the body to a sealing end, wherein the body includes a pocket formed at the sealing end having a depth; a collet secured to an outer surface of the tube and having a first end; and a polymer seal having a channel to pass a fluid, the polymer seal including a flange portion and an insertion portion; locating the insertion portion of the polymer seal into the pocket of the body of the tube so that a gap exists between the end of the tube and the flange portion prior to compression by the compression screw; compressing, by the compression screw being rotated about the coupling body, the polymer seal between the tube and the sealing surface of the coupling body; and forming a fluidic seal between the endface of the tube and the flange portion after the compressing.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

DETAILED DESCRIPTION

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

In brief overview, the invention relates to a tube fitting and connection system to facilitate secure, low leak rate fluid flow through a junction of fluidic paths in a chemical analysis instrument such as a liquid chromatography system. The device allows fluid containing various mixtures of chemical samples to pass through the junction of the fluidic paths at high pressure with little or no trapped residue remaining in the connection. Trapped residue is an undesirable condition present in many high pressure liquid connections and can lead to degradation in performance of the analytical instrument. According to various embodiments, the device provides a face seal between two separate fluidic path features. Fluidic paths can be in the form of cylindrical tubes or passages drilled or otherwise created in solid structures for the management of fluid. Sealing of fluidic paths can be aided by the use of compliant polymer seals which facilitate intimate contact between adjacent surfaces. Intimate contact significantly limits or prevents the entry of fluids under high pressure into volumes that are not directly in the fluid flow. Thus the risk of a fluid, such as a chemical sample, entering an unswept or trapped volume near the sealing features is reduced or eliminated.

Figure 1:
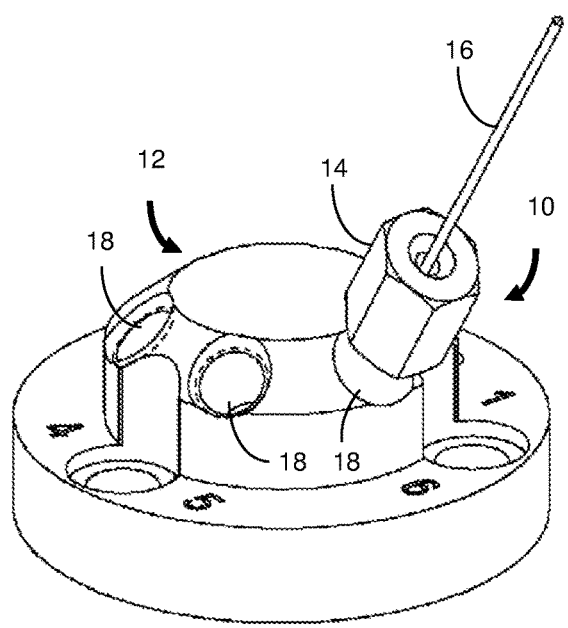
FIG. 1 is an illustration of a fluidic coupling for a rotary shear seal valve in a liquid chromatography system.

By way of example, FIG. 1 shows a view of a fluidic coupling 10 at the interface of a sample loop and a stator portion 12 of a rotary shear seal valve for a liquid chromatography system. The coupling 10 includes a compression nut 14 and other components (not visible). A tube 16 defines a fluidic path that conducts a fluid from a sample source to a stator port 18 at the coupling 10 or from the stator port 18 to a chromatographic column. A second fluidic path is present inside the stator portion 12 and interfaces with a rotor that couples, or decouples, the second fluidic path with another fluidic path that communicates with one of the other stator ports 18.

Figure 2B:
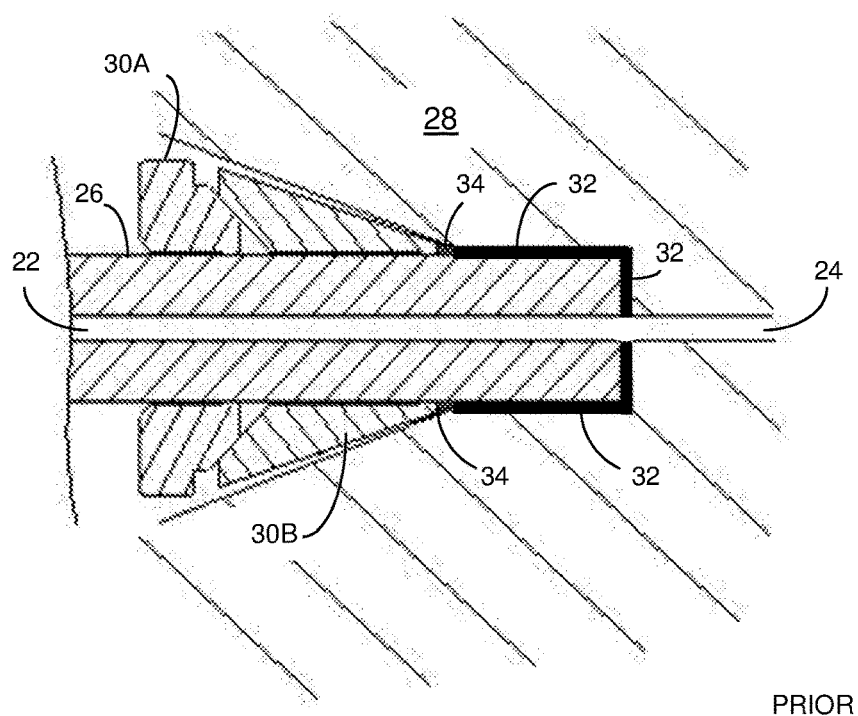
FIG. 2B is an expanded view of a portion of FIG. 2A that shows the sealing interface.
Figure 2A:
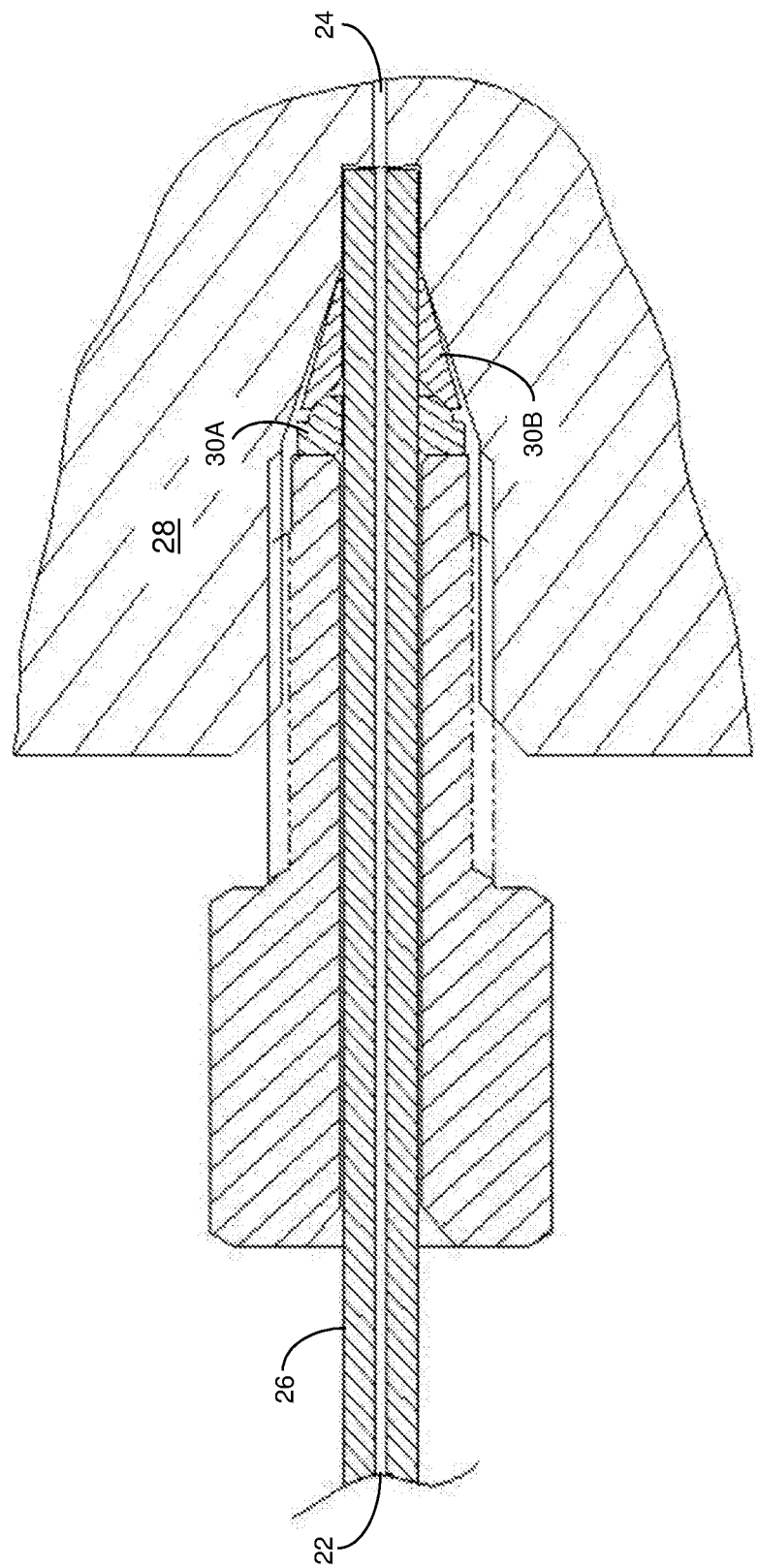
FIG. 2A a cross-sectional view of a conventional compression fitting for coupling two fluidic paths.

FIG. 2A shows a cross-sectional view of a conventional fitting 20 that can be used, for example, to couple two fluidic paths 22 and 24. For example, the fitting 20 can be used to couple the tube 16 of FIG. 1 to an internal fluidic path in the rotary shear seal valve. Tube 26 includes the first fluidic path 22 which is coupled to the second fluidic path 24 at a bottom surface of a coupling body 28. FIG. 2B is an expanded view of a portion of FIG. 2A that shows the sealing interface. A two-part ferrule 30A and 30B engages an inner tapered surface of the coupling body 28 and the outer diameter of the tube 26. The resulting fluidic seal can withstand a high fluid pressure (e.g., greater than 15,000 psi); however, an unswept volume (designated by the thick black lines 32 and the region to the right of the contact zone 34 between ferrule part 30B and the tapered surface) can exist and may result in sample carryover. For example, as the sample moves past the unswept volume 32, some of the sample may diffuse into the volume 32. The sample in the unswept volume 32 can subsequently diffuse back into the main fluid flow in fluidic path 24. If the fitting 20 is used with components of a liquid chromatography system, such as illustrated in FIG. 1, the fluid sample that diffuses back into the fluid flow (i.e., the carryover) can adversely affect chromatographic results.

Figure 3A:
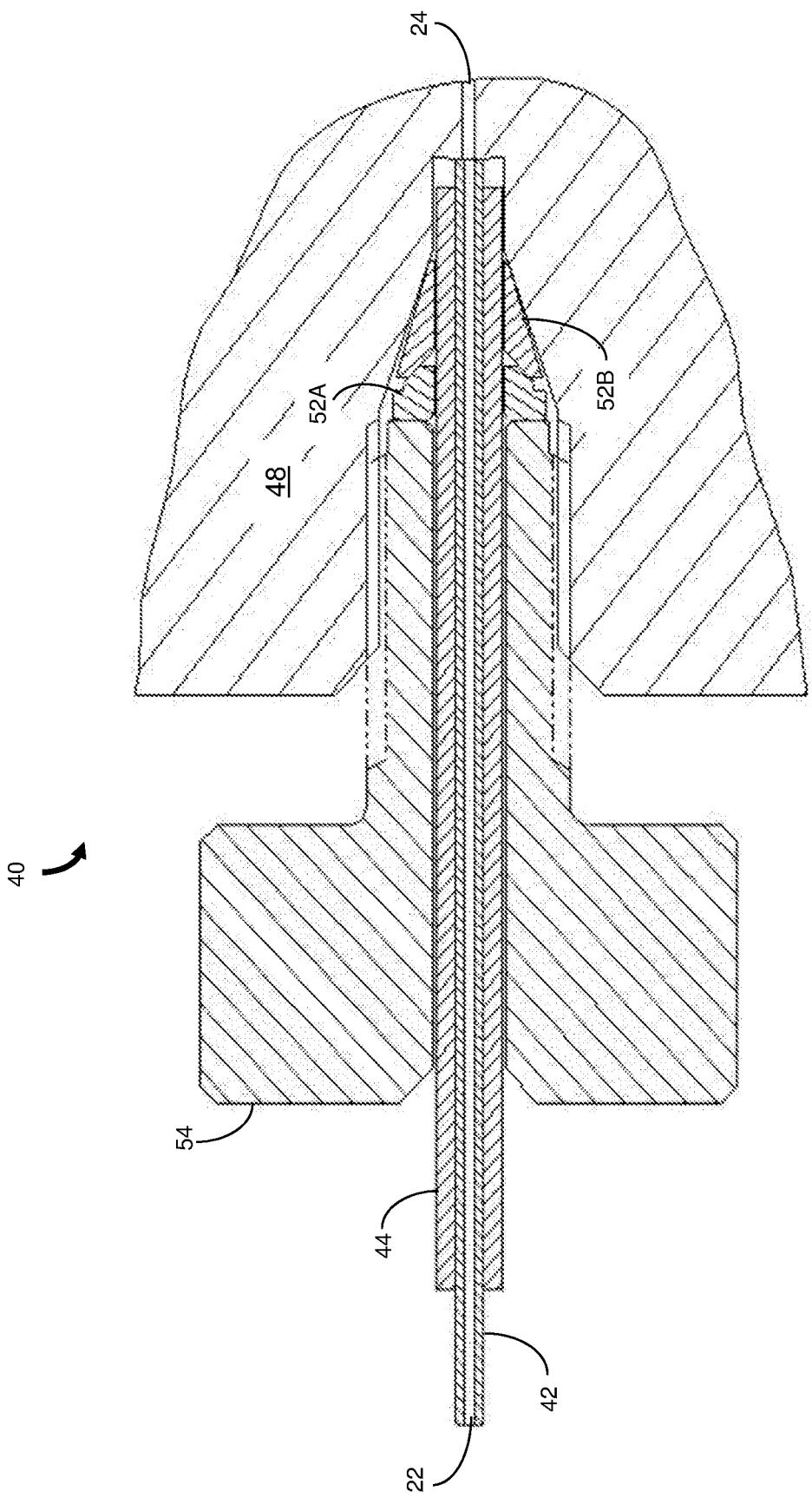
FIG. 3A is a cross-sectional view of a fitting for coupling fluidic paths according to an embodiment of the invention.
Figure 3B:
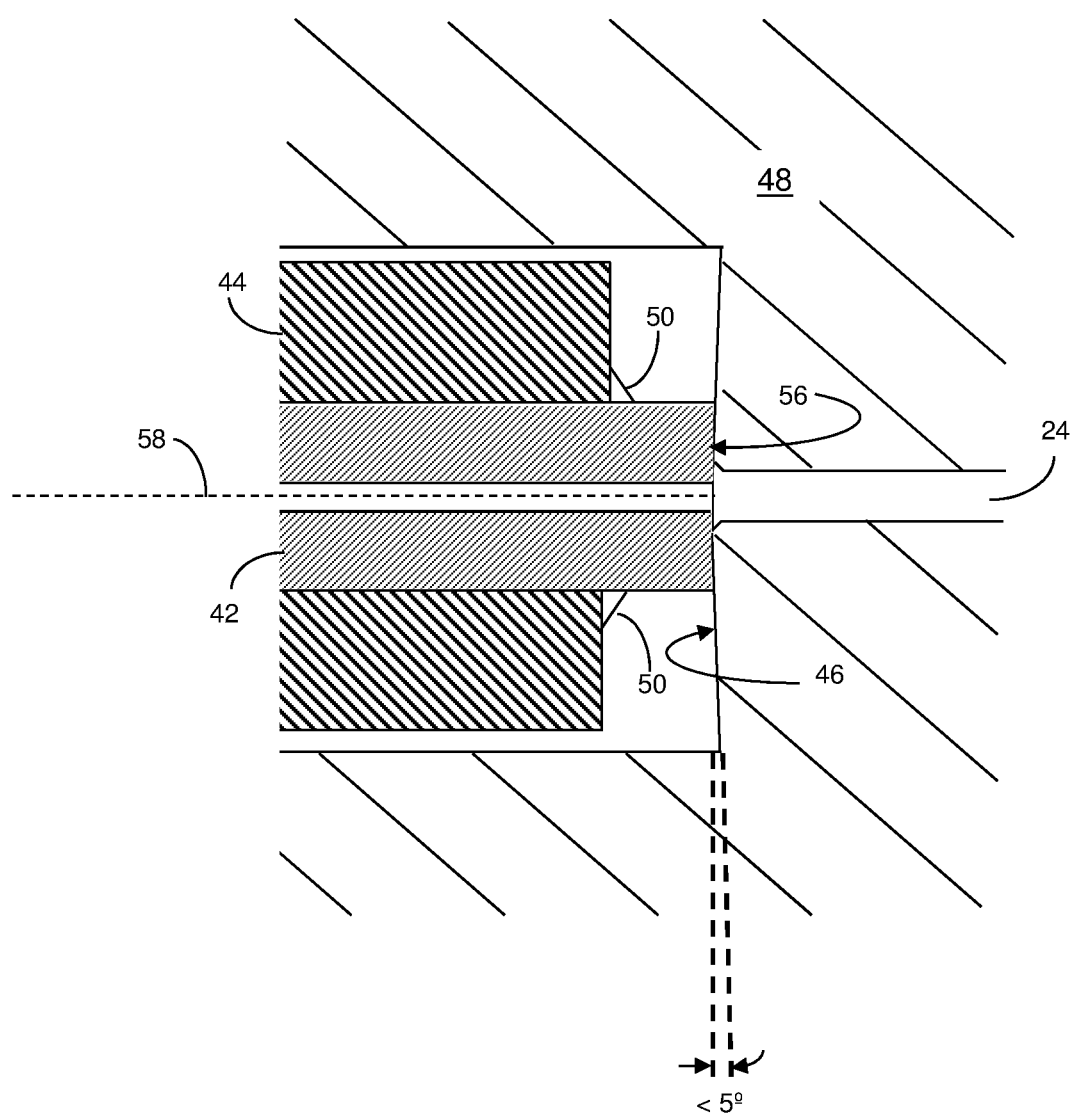
FIG. 3B is an expanded cross-sectional view of the fitting of FIG. 3A in a region of the face seal.

FIG. 3A is a cross-sectional view of an embodiment of a fitting 40 for coupling fluidic paths according to the invention. FIG. 3B is an expanded cross-sectional view of the fitting 40 in a region where a face seal is created. The fitting 40 includes a tube assembly having a stainless steel tube 42 surrounded over a portion of its length by a stainless steel sleeve 44. The tube 42 and sleeve 44 are joined at the end of the sleeve 44 with the tube 42 protruding a sufficient length (e.g., 0.015 in.) to allow it to contact a sealing surface 46 of a coupling body 48. In a preferred embodiment, the tube 42 and sleeve 44 are joined by a weld 50. The weld 50 may be, for example, a laser weld or an electron beam weld as are known in the art. By way of a specific dimensional example, the inner and outer diameters of the stainless steel tube 42 can be 0.004 in. and 0.025 in., respectively, the outer diameter of the sleeve 44 can be 0.062 in. and the diameter of the second fluid path 24 in the coupling body 48 can be 0.006 in.

The tube assembly is encircled by a two-part compression member 52A and 52B (generally 52) in a tapered cavity of the coupling body 48. For example, the compression member 52 can be a stainless steel ferrule set (e.g., part no. SS-100-SET available from Swagelok Company of Solon, Ohio). A compression screw 54 having threads that engage threads in an upper portion of the coupling body 48 is used to force the compression member 52 against the surface of the tapered cavity. The force causes the compression member 52 to grip the sleeve 44 and force the tube assembly into intimate contact with the sealing surface 46 of the coupling body 48. Preferably, the sealing surface 46 has a weak conical form (e.g., the surface 46 departs from a flat surface by less than 5°) to thereby reduce the surface area of the end face 56 of the stainless steel tube 42 that contacts the sealing surface 46. The end face 56 of the stainless steel tube 42 is substantially normal to the longitudinal axis 58 of the tube 42 and has a low surface roughness (e.g., flat to within 0.000032 in.). As long as the compression screw 54 maintains forceful contact with the compression member 52, and therefore the tube assembly, a tight fluid seal is maintained between the end face 56 of the protruding tube 42 and the sealing surface 46 of the coupling body 48.

Figure 4:
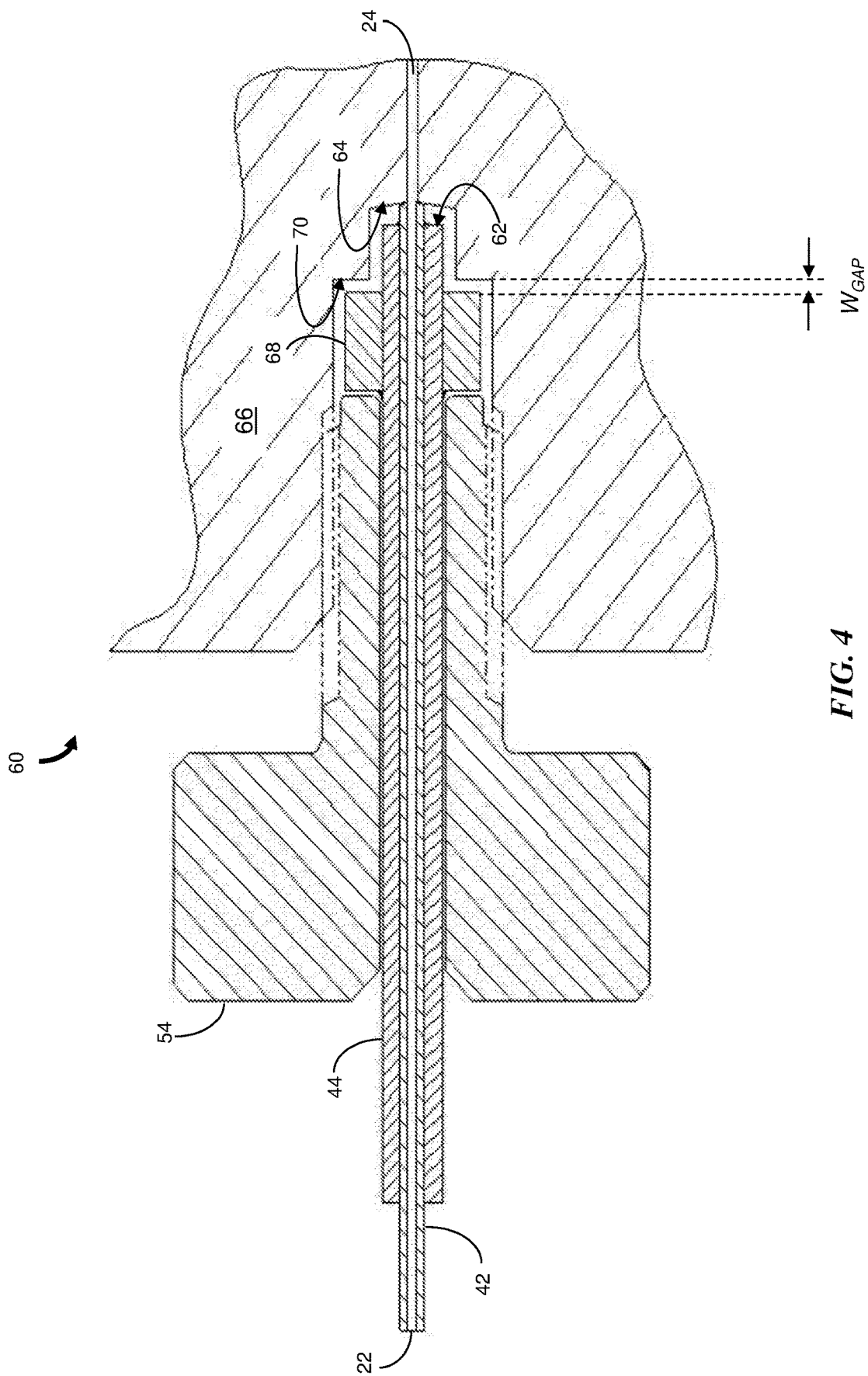
FIG. 4 is a cross-sectional view of a fitting for coupling fluidic paths according to another embodiment of the invention.

FIG. 4 is a cross-sectional view of a fitting 60 according to another embodiment of the invention. The fitting 60 includes a stainless steel tube assembly similar to that shown in FIGS. 3A and 3B. The end face 62 of the stainless steel tube 42 is tapered to form a shallow male cone which engages a female cone of slightly different angle formed in the sealing surface 64 of the coupling body 66. Although other cone angles are possible, by way of a specific numerical example, the shallow male cone can have a cone angle of 139° and the cone angle of the sealing surface 64 can be 140°.

A collet 68, or bushing, is attached to the outer surface of the stainless steel sleeve 44 by welding or other suitable attachment method. A threaded compression screw 54 engages threads in the coupling body 66 to apply compressive force to the tube assembly by means of the attached collet 68. The compressive force urges the tapered end face 62 of the stainless steel tube 42 against the tapered sealing surface 64 of the coupling body 66. The force is sufficient to create and maintain intimate contact between the end face 62 and sealing surface 64, thereby creating a secure fluidic seal. A bore end surface 70 at one end of a larger bore of the coupling body 66 is configured to receive an end of the welded collet 68. Once the compression screw 54 is rotated sufficiently so that the welded collet 68 traverses an initial gap of width WGAP and makes contact with the bore end surface 70, the subsequent resistance encountered prevents a user from further tightening the compression screw 54. This restriction prevents damage to the tapered end face 62, protruding portion of the stainless steel tube 42 and the tapered sealing surface 64 that might otherwise occur to the effectiveness of the fluidic seal.

In various embodiments, the taper angle and size of the formed end face 62 can be adjusted to obtain a suitable contact at the interface of the end face 62 and the sealing surface 64 of the coupling body 66 to achieve an acceptable fluidic seal for varying conditions of pressure and flow.

Figure 5A:
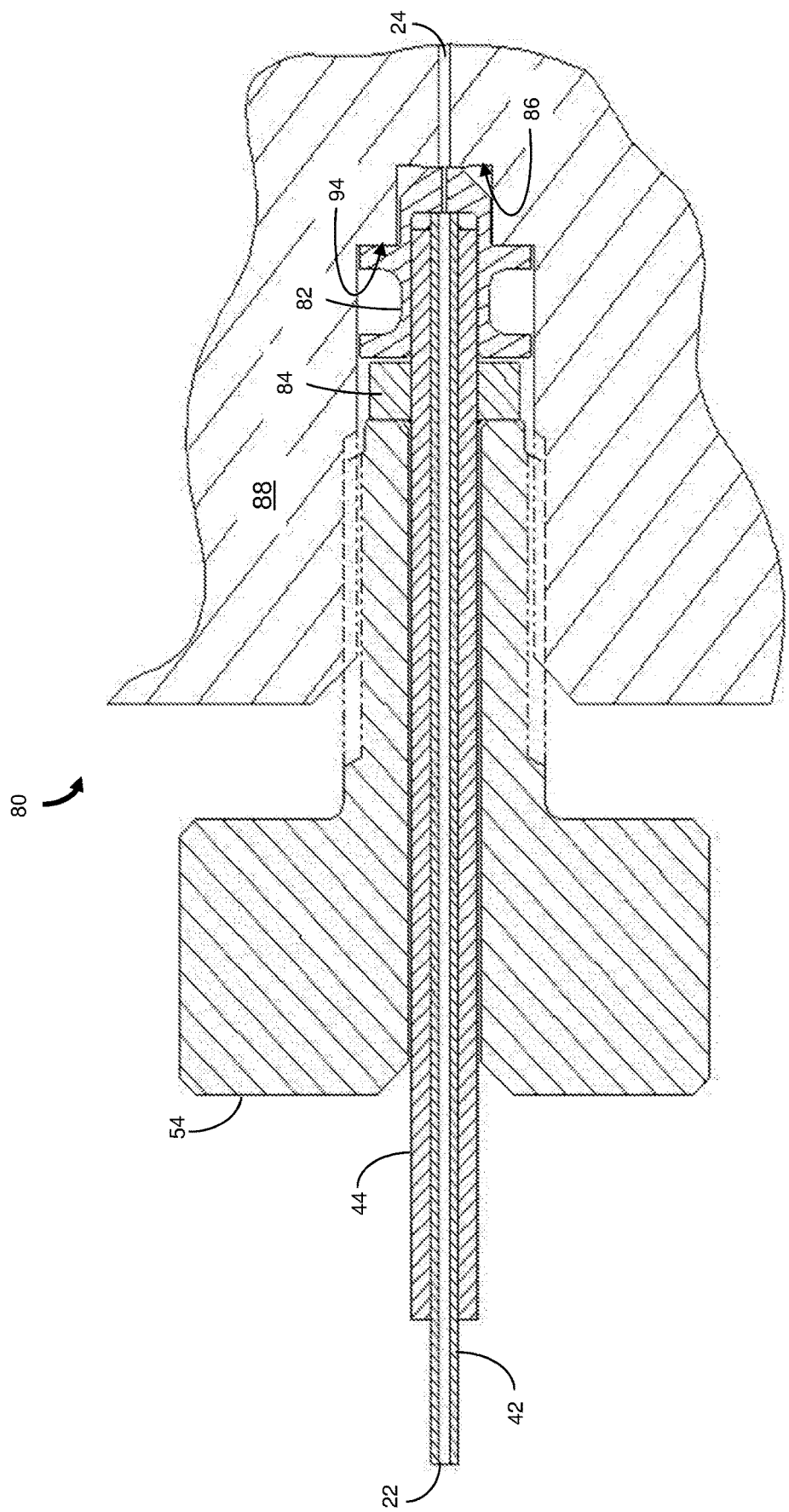
FIG. 5A is a cross-sectional view of a fitting for coupling fluidic paths according to another embodiment of the invention.
Figure 5B:
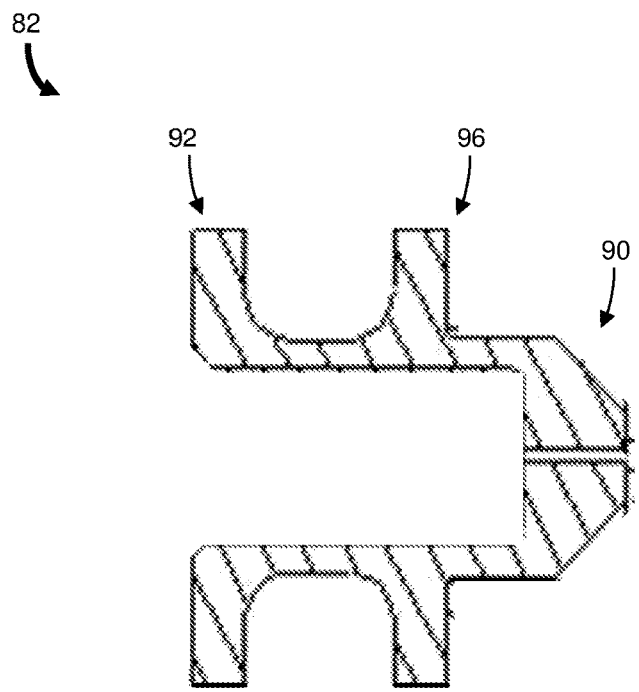
FIG. 5B is a detailed illustration of the polymer seal in the fitting of FIG. 5A.

FIG. 5A is a cross-sectional view of a fitting 80 according to another embodiment of the invention. The fitting 80 has a similar configuration to the fitting of FIG. 4; however, a polymer seal 82 (or polymer gasket), shown in more detail in FIG. 5B, is provided to encircle and substantially enclose the end of the tube assembly. The polymer seal 82 includes a lower seal portion 90 and first and second upper seal portions 92 and 96. The lower seal portion 90 has a smaller diameter than the upper seal portions 92, 96.

During insertion of the tube assembly into the coupling body 88, an initial gap exists between the end of the lower seal portion 90 and a sealing surface 86 of the narrow bore. As the compression screw 54 is turned, the polymer seal is 82 urged forward into the coupling body 88 to close the gap and then to engage the sealing surface 86. Additional rotation of the compression screw 54 compresses the lower seal portion 90 so that it conforms to the end of the stainless steel tube 42 and the sealing surface 86 to create a secure fluidic seal. Once the collet engages the first upper seal portion 92, further rotation urges the tube assembly, collet 84 and polymer seal 82 deeper into the coupling body 88 until the second upper seal portion 96 comes into contact with a bottom surface 94 of a larger bore. The upper seal portions 92, 96 are larger in dimension and therefore less compliant and allow only a small amount of additional compressive deformation of the polymer seal 82. Thus further rotation of the compression screw 54 is resisted and the bottom surface 94 of the larger bore acts as a stop to limit the amount of force applied to the stainless steel tube 42 and the sealing surface 86 of the narrow bore. Advantageously, the total fitting force applied by the compression screw 54 does not overload the seal interface and the polymer seal 82.

In various embodiments, the shape, angle and size of the polymer seal 82 features are modified to obtain a suitable seal interface under varying conditions of pressure and flow. The polymer material may be selected to provide suitable mechanical properties and chemical compatibility. In one embodiment, the polymer seal 82 is a Dupont Vespel® SCP-5000 polyimide gasket.

Alternative embodiments to the illustrated fitting 80 are contemplated. For example, one such embodiment utilizes a one-piece "plain tube" (i.e., a tube without a sleeve) having a tapered end face in place of the welded tube assembly.

Figure 6B:
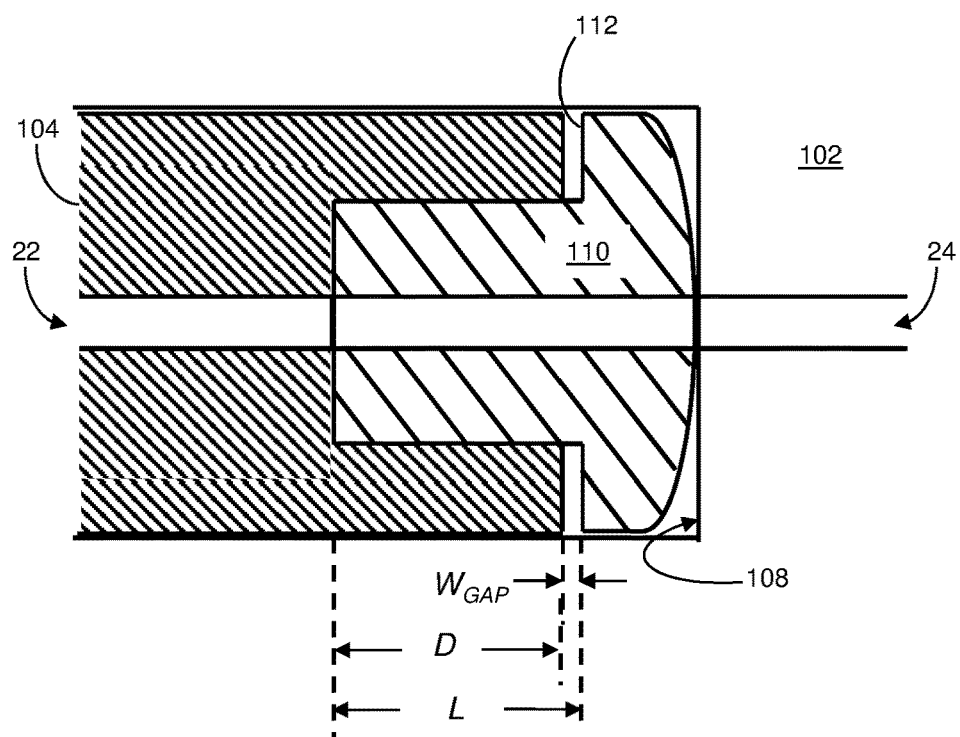
FIG. 6B is an illustration showing an expanded view of the sealing interface region of FIG. 6A.
Figure 6A:
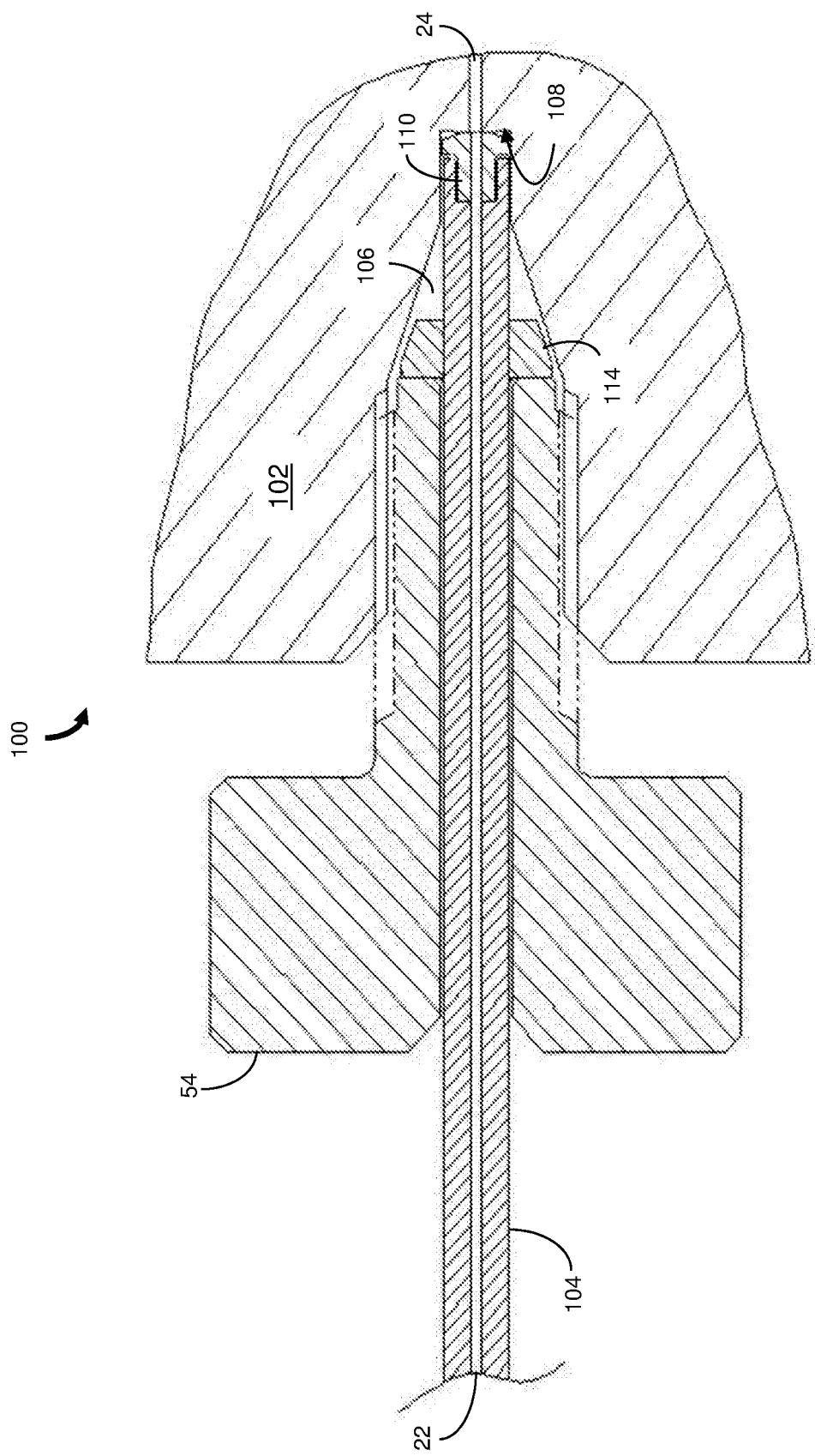
FIG. 6A is a cross-sectional view of a fitting for coupling fluidic paths according to another embodiment of the invention.

FIG. 6A is a cross-sectional view of a fitting 100 according to another embodiment of the invention. The fitting 100 includes a coupling body 102 having a threaded bore that receives a compression screw 54. The threaded bore opens into a tapered cavity 106. A narrow bore extending from the narrow end of the tapered cavity 106 includes a flat sealing surface 108. A single piece stainless steel tube 104 includes the fluidic channel 22 to be coupled to the fluidic channel 24 in the coupling body 102. The stainless steel tube 104 includes a pocket of depth D formed at its sealing end occupied by part of a stem portion of length L of a polymer seal 110.

FIG. 6B shows an expanded view of the region in which the fluidic paths 22, 24 are coupled. Referring to FIG. 6A and FIG. 6B, the polymer seal 110 is shaped so that when inserted without compression into the pocket, an initial gap of width WGAP exists between the end of the tube 104 and a flange portion 112 of the seal 110. The flange portion 112 extends radially outward to the outer diameter of the tube 104. A collet 114 having a tapered surface is secured to the tube 104 by welding or other appropriate attachment method. A threaded compression screw 54 is used to apply a compressive force to the tube 104 by means of a threaded bore in the coupling body 102 and the attached collet 112 in a manner similar to that described in the above embodiments. As the force is applied, the polymer seal 110 is pushed into intimate contact with the sealing surface 108 to create a secure fluidic seal. The initial gap between the end of the tube 104 and the flange portion 112 allows the polymer seal 110 to compress by an amount sufficient to create the fluidic seal. After sufficient force is applied to compress the polymer seal 110 and eliminate the gap, further force causes the end of the tube 104 to come into contact with the less compliant flange portion 112. Thus only a small amount of additional compressive deformation of the polymer seal 110 occurs at a much lower deformation rate and higher force level. As a result, the total force that can be applied to the sealing end of the stainless steel tube 104 is limited, ensuring that the total fitting force applied by the compression screw 54 does not overload the polymer seal 110 and damage the sealing surface 108.

In other embodiments, the shape and dimensions of the features of the polymer seal 110 are modified to obtain a suitable fluidic seal under varying conditions of pressure and flow. The polymer material can be selected to provide suitable mechanical properties and chemical compatibility. In one embodiment, the polymer seal 110 is a Dupont Vespel® SCP-5000 polyimide gasket.

While the invention has been shown and described with reference to specific embodiments, it should be understood by those skilled in the art that various changes in form and detail may be made therein without departing from the spirit and scope of the invention as recited in the accompanying claims.

What is claimed is:

1. A fitting for coupling fluidic paths, comprising:
a coupling body having a threaded bore extending into a tapered cavity and, and an inner bore extending from the tapered cavity that is narrower than the threaded bore, the inner bore having a sealing surface at an end opposite to the tapered cavity, the coupling body having a channel extending from the sealing surface to pass a fluid;
a compression screw having an axial bore, a threaded portion in engagement with the threaded bore of the coupling body, and a drive surface;
a tube extending through the axial bore of the compression screw, the tube including a body and a fluidic channel extending through the body to a sealing end, wherein the body includes a pocket formed at the sealing end having a depth;
a collet secured to an outer surface of the tube and having a first end configured to receive the drive surface of the compression screw; and
a polymer seal having a channel to pass a fluid, the polymer seal including a flange portion and an insertion portion, wherein the insertion portion is located within the pocket of the body of the tube.

2. The fitting of claim 1, wherein the body of the tube is a single piece stainless steel tube.

3. The fitting of claim 1, wherein the flange portion of the polymer seal extends radially outward to an outer diameter of the outer surface of the tube.

4. The fitting of claim 1, wherein the collet includes a tapered surface that is configured to contact an inner surface of the tapered cavity of the coupling body.

5. The fitting of claim 4, wherein the collet is secured to the outer surface of the tube by welding.

6. The fitting of claim 1, wherein rotation of the compression screw about the coupling body is configured to apply a compressive force to the tube and the collet and push the polymer seal into intimate contact with the sealing surface to create the fluidic seal.

7. The fitting of claim 6, wherein a gap exists between the end of the tube and the flange portion prior to compression by the compression screw, wherein a fluidic seal is formed between the endface of the tube and the flange portion after compression by the compression screw, wherein the gap allows the polymer seal to compress by an amount sufficient to create the fluidic seal, and wherein the compressive force eliminates the gap during compression and causes the sealing end of the tube to come into contact with the flange portion of the polymer seal.

8. A fluidic coupling comprising:
a compression screw having an axial bore, a threaded portion configured to engage a threaded bore of a coupling body, and a drive surface;
a tube extending through the axial bore of the compression screw, the tube including a body and a fluidic channel extending through the body to a sealing end, wherein the body includes a pocket formed at the sealing end having a depth;
a collet secured to an outer surface of the tube and having a first end configured to receive the drive surface of the compression screw; and
a polymer seal having a channel to pass a fluid, the polymer seal including a flange portion and an insertion portion, wherein the insertion portion is located within the pocket of the body of the tube.

9. The fluidic coupling of claim 8, wherein the body of the tube is a single piece stainless steel tube.

10. The fluidic coupling of claim 8, wherein the flange portion of the polymer seal extends radially outward to an outer diameter of the outer surface of the tube.

11. The fluidic coupling of claim 8, wherein the collet includes a tapered surface that is configured to contact an inner surface of the tapered cavity of the coupling body.

12. The fluidic coupling of claim 11, wherein the collet is secured to the outer surface of the tube by welding.

13. The fluidic coupling of claim 8, wherein the compression screw is configured to apply a compressive force to the tube and the collet and push the polymer seal into intimate contact with the sealing surface to create the fluidic seal.

14. The fluidic coupling of claim 13, wherein a gap exists between the end of the tube and the flange portion prior to compression by the compression screw, wherein a fluidic seal is formed between the endface of the tube and the flange portion after compression by the compression screw, wherein the gap allows the polymer seal to compress by an amount sufficient to create the fluidic seal, and wherein the compressive force eliminates the gap during compression and causes the sealing end of the tube to come into contact with the flange portion of the polymer seal.

15. A method comprising:
providing a fitting for coupling fluidic paths, the fitting including:
a coupling body having a threaded bore extending into a tapered cavity and, and an inner bore extending from the tapered cavity that is narrower than the threaded bore, the inner bore having a sealing surface at an end opposite to the tapered cavity, the coupling body having a channel extending from the sealing surface to pass a fluid;
a compression screw having an axial bore, a threaded portion in engagement with the threaded bore of the coupling body, and a drive surface;
a tube extending through the axial bore of the compression screw, the tube including a body and a fluidic channel extending through the body to a sealing end, wherein the body includes a pocket formed at the sealing end having a depth;
a collet secured to an outer surface of the tube and having a first end; and
a polymer seal having a channel to pass a fluid, the polymer seal including a flange portion and an insertion portion;
locating the insertion portion of the polymer seal into the pocket of the body of the tube;
compressing, by the compression screw being rotated about the coupling body, the polymer seal between the tube and the sealing surface of the coupling body; and
forming a fluidic seal between the endface of the tube and the flange portion after the compressing.

16. The method of claim 15, further comprising receiving, by the first end of the collet, the drive surface of the compression screw during compression.

17. The method of claim 16, further comprising:
applying, by the compression screw, a compressive force to the tube and the collet during the compressing; and
pushing, by the compression screw, the polymer seal into intimate contact with the sealing surface to create the fluidic seal.

18. The method of claim 17, wherein a gap exists between the end of the tube and the flange portion prior to compression by the compression screw, the method further comprising allowing, by the gap of the polymer seal, the polymer seal to compress by an amount sufficient to create the fluidic seal.

19. The method of claim 18, further comprising eliminating, with the compressive force, the gap during compression and causing the sealing end of the tube to come into contact with the flange portion of the polymer seal.

20. The method of claim 19, further comprising:
- limiting the total force that can be applied to the sealing end of the tube by the gap and the flange portion; and
- ensuring that the total fitting force applied by the compression screw does not overload the polymer seal and damage the sealing surface.

\* \* \* \* \*